(12) United States Patent
Ranby (10) Patent No.: US 6,368,785 B1
(45) Date of Patent: Apr. 9, 2002

(54) ANTI-COAGULATION OF BLOOD, PLASMA OR SYNOVIAL FLUID PRODUCTS USING ISO-CITRATE

(75) Inventor: Mats Ranby, Linkoping (SE)

(73) Assignee: Global Hemostasis Institute MGR AB, Linkoping (SE)

(*) Notice: Subject to any disclaimer, the term of this patent is extended or adjusted under 35 U.S.C. 154(b) by 0 days.

(21) Appl. No.: 09/453,065

(22) Filed: Dec. 2, 1999

Related U.S. Application Data (63) Continuation of application No. PCT/SE98/01030, filed on May 29, 1998.
(60) Provisional application No. 60/052,929, filed on Jun. 5, 1997.

(51) Int. Cl.[7] .................................................. A01N 1/02
(52) U.S. Cl. ............................................................ 435/2
(58) Field of Search ................................................ 435/2

(56) References Cited

U.S. PATENT DOCUMENTS

| | | | | |
|---|---|---|---|---|
| 4,828,976 A | * | 5/1989 | Murphy ........................ | 435/2 |
| 5,175,087 A | | 12/1992 | Ranby et al. .................. | 435/2 |

FOREIGN PATENT DOCUMENTS

| | | | |
|---|---|---|---|
| AU | 6554464 | * | of 1968 |
| DE | 0 244 834 A3 | | 6/1987 |
| GB | WO 88/08004 | | 10/1988 |

OTHER PUBLICATIONS

Vox Sanguinis, (1999)76:67–77, "Liquid–Stored Red Blood Cells for Transfusion", A Status Report, C.F. Hogman.

* cited by examiner

*Primary Examiner*—Sandra E. Saucier
(74) *Attorney, Agent, or Firm*—Bacon & Thomas (57) ABSTRACT

A method of anti-coagulating a blood, blood plasma or synovial fluid product comprising addition to the product iso-citrate is described. The method may further comprise adjustment of the calcium ion activity of the anti-coagulated product to physiological levels with a soluble calcium salt. Blood, blood plasma or synovial fluid products containing an anti-coagulating amount of anti-coagulant comprising iso-citrate, and optionally citrate, is disclosed. These anti-coagulated products are used for transport and storage of the products and/or for analysis of hemostatic or coagulative properties of the products. Additionally, blood sampling containers comprising isotonic or slightly hypertonic solutions of iso-citrate, and blood sampling containers comprising a solution of 0.1–0.5 M iso-citrate in one tenth of the container volume, and optionally an effective amount of calcium chloride resulting in a calcium ion activity of approximately 1 mM, are disclosed. Finally, reagents for analysis of blood, blood plasma or synovial fluid products comprising iso-citrate are described.

8 Claims, 8 Drawing Sheets

ANTI-COAGULATION OF BLOOD, PLASMA OR SYNOVIAL FLUID PRODUCTS USING ISO-CITRATE

This application is a continuation of pending international application number PCT/SE98/01030 filed May 29, 1998 (of which the entire disclosure of the pending, prior application is hereby incorporated by reference), which claims benefit of U.S. provisional application No. 60/052,929 filed Jun. 5, 1997, benefit for this application is also claimed under 35 USC 119(e).

The present invention relates to a method of anti-coagulating blood, blood plasma or synovial fluid products with moderately calcium binding anti-coagulants, and optionally adjusting the calcium ion activity up to physiological levels with a soluble calcium salt.

BACKGROUND

Biological fluids, in particular blood, lymph, synovial fluid and cerebral liquor and cell free preparations of these, e.g. blood plasma, can undergo drastic changes in rheological, i.e. visco-elastic, properties. The fluids can change from a liquid having rheological properties similar to water, to a gel having rheological properties more like cottage cheese. The described rheological transition, commonly denoted coagulation or clotting, can occur when the biological fluid is removed from its natural environment and is collected in some man-made container.

To prevent coagulation upon collection of biological fluid, some substance with coagulation-inhibiting properties may need to be added. Substances used to inhibit coagulation, also called anti-coagulants, include oxalate, EDTA, citrate, heparin and hirudin. These anti-coagulants either cause specific inhibition of enzymes involved in coagulation or modify conditions within the biological fluid so that the coagulative processes are unable to proceed. These conditions include free calcium ion concentration, also called $Ca^{2+}$ activity, and pH.

According to prior art theory, the mechanism of action for some of the anti-coagulants is to form complexes with $Ca^{2+}$ ions and thereby reduce the levels of free $Ca^{2+}$, i.e. reduce the $Ca^{2+}$ activity, in a biological fluid to non-effective levels. It is thereby understood that the $Ca^{2+}$ activity is required at a certain level for the coagulation processes to proceed. The present invention pertains particularly to anti-coagulants of this later kind when coagulation is hampered when $Ca^{2+}$ activity is below 0.8 mM or the pH is below 7.

If the biological fluid is anti-coagulated by reduction of the $Ca^{2+}$ activity, then the biological fluid can be brought back to a coagulable state by the addition of $Ca^{2+}$, e.g. in the form of a $CaCl_2$ solution, to restore the $Ca^{2+}$ activity to coagulation-permitting levels.

The procedure of anti-coagulating a biological fluid in a reversible manner, i.e. in a manner that allows a return of the fluid to a coagulation-permitting state, is common, and necessary, for analysis of the coagulation activity of the fluid. Oxalate, EDTA and citrate are examples of anti-coagulants that, according to prior art, function by reducing the $Ca^{2+}$ activity in the biological fluid. Further, according to prior art, any substance that sufficiently reduces $Ca^{2+}$ activity of a biological fluid will function as an anti-coagulant.

According to prior art, all substances that function as anti-coagulants by reduction of the $Ca^{2+}$ activity form relatively stabile $Ca^{2+}$ complexes which are characterized by apparent dissociation constants of 0.5 mM or less. Citrate, for example, which together with EDTA is the most commonly used anticoagulant of this kind, forms $Ca^{2+}$ complexes with an apparent dissociation constant at physiological conditions of about 0.4 mM. The $Ca^{2+}$ EDTA complexes and $Ca^{2+}$ oxalate complexes are considerably tighter.

As discussed above, analysis of coagulation analytes in biological fluids are commonly performed on citrate anti-coagulated samples. By virtue of its relatively low affinity for $Ca^{2+}$ and by use of minimal amounts, anti-coagulation with citrate is considered to be gentle with regard to causing denaturation and destabilization of proteins and lipid-protein structures of the biological fluid. Still, it may be assumed, that citrate anti-coagulation has some adverse effects. Factor VIII, for example, is less stabile in citrated blood and blood plasma than in the circulation. Also the results of activated prothrombin time (APTT) analysis of citrated blood or blood plasma displays limited stability. Thus, according to prior art, some coagulatory analytes display a degree of instability that necessitates special considerations in clinical laboratory routines. These more rigorous routines add costs and inconvenience to medical laboratory procedures.

When analyzing an anti-coagulated sample of a biological fluid for various coagulatory activities, the sample is mixed with reagents which include $Ca^{2+}$. The amount of added $Ca^{2+}$ is sufficient to give the reaction mixture a $Ca^{2+}$ in the range of 0.8 to 8 mM at which conditions the coagulatory activities are displayed.

Although commonly used, the procedure of first anti-coagulating a sample of biological fluid by reduction of $Ca^{2+}$ activity is undesirable in some respects. For example, denaturation and destabilization of the structures of interest as discussed above. Further, it is impossible, in a given procedure, to exactly balance out the effects of added anti-coagulant by addition of $Ca^{2+}$. The $Ca^{2+}$ of the recalcified sample is likely to be different from the native fluid, and in a series of samples of such a fluid, the variation in $Ca^{2+}$ activity is likely to be greater than the variation in the original native fluid. This deviation from the native levels, also denoted physiological levels, of $Ca^{2+}$ activity displayed in recalcified biological fluids most likely has undesirable influence on coagulation assay systems and their results.

A related medical field in which anti-coagulation by reduction of $Ca^{2+}$ causes practical concerns is blood banking. Blood or blood plasma that is to be used in transfusion is commonly anti-coagulated. This is because, with present techniques, native blood and blood plasma can only be handled for a short time period outside the organism without coagulating.

Because of low toxicity, rapid metabolization and relatively good anti-coagulant properties, citrate is the commonly used anticoagulant in blood banking. In many cases, the citrate content in transfused blood or blood plasma does not cause adverse effects for the receiving patient. But in some cases, especially in patients with liver dysfunction, citrate anti-coagulated blood and blood plasma are not well tolerated. Due to slow metabolism of citrate in these patients, the citrate causes a notable reduction in $Ca^{2+}$ activity which results in cramps and gastrointestinal discomfort.

There is a need for an improved method of anti-coagulating blood, blood plasma and synovial fluid products to improve the properties of the products for such applications as transport and storage of the products, use of the products for transfusion purposes and analysis of hemostatic or coagulative properties of the products.

DESCRIPTION OF THE INVENTION

The present invention provides a method of anti-coagulating a blood, blood plasma or synovial fluid product.

The method comprises addition of iso-citrate and optionally a soluble calcium salt.

The method of the invention is for example useful for accomplishing 1) increased stability and reduced denaturation of coagulation analytes in the anti-coagulated product, 2) closer to physiological levels of $Ca^{2+}$ activity and decreased variation in $Ca^{2+}$ activity of assay systems for coagulation analytes, and 3) reduction in the $Ca^{2+}$ lowering effect when citrate anti-coagulated blood or blood plasma is transfused into patients.

Thus, one aspect of the invention is directed to a method of anti-coagulating a blood, blood plasma or synovial fluid product comprising the step of adding to the product an effective amount of iso-citrate.

In an embodiment of this aspect of the invention the method additionally comprises the step of adjusting the calcium ion activity of the anti-coagulated product up to physiological levels with a soluble calcium salt.

In this context it can be mentioned that the calcium ion activity of the anti-coagulated product of the invention can be reduced by the addition of citrate or other calcium binding substance and that the pH can be adjusted for specific purposes.

In a preferred embodiment of this aspect of the invention the effective amount of iso-citrate is 5–50 mmol per liter of blood product or 7–70 mmol per liter of blood plasma or synovial fluid product, and in a most preferred embodiment the amount of iso-citrate is 15–25 mmol per liter of blood product or 2–35 mmol per liter of blood plasma or synovial fluid product.

Another aspect of the invention is directed to a blood, blood plasma or synovial fluid product containing an anti-coagulating amount of anti-coagulant comprising iso-citrate. In an embodiment of this aspect of the invention the anti-coagulant comprises citrate, in addition to iso-citrate.

In a preferred embodiment of this aspect of the invention the anti-coagulating amount of iso-citrate is 5–50 mmol per liter of blood product or 7–70 mmol per liter of blood plasma or synovial fluid product, and in a most preferred embodiment anti-coagulating amount of iso-citrate is 15–25 mmol per liter of blood product or 25–35 mmol per liter of blood plasma or synovial fluid product.

A further aspect of the invention is directed to the use of a blood, blood plasma or synovial fluid product according to the invention for transport and storage of the product. The transported and stored blood, blood plasma or synnovial fluid product may then be used directly for transfusion into patients.

Yet another aspect of the invention is directed to the use of a blood, blood plasma or synovial fluid product according to the invention for analysis of hemostatic or coagulative properties of the product, i.e. for diagnostic purposes.

Still another aspect of the invention is directed to a blood sampling container comprising an isotonic or slightly hypertonic solution of iso-citrate.

Another embodiment of a blood sampling container of the invention comprises a solution of 0.1–0.5 M iso-citrate in one tenth of the container volume.

The blood sampling containers according to the invention may additionally comprise, together with the iso-citrate, an effective amount of calcium chloride resulting in a calcium ion activity of up to approximately 1 mM.

The blood sampling containers of the invention are preferably conventional, optionally evacuated, test tubes, syringes or plastic bags used in the handling of blood and blood plasma products, and are ready for delivery to laboratories responsible for blood sampling and analysis.

Yet another aspect of the invention is directed to reagents for analysis of blood, blood plasma or synovial fluid products comprising iso-citrate. The reagents are provided in containers with labels and instructions for use.

DESCRIPTION OF EXPERIMENTS

Materials and Methods

Activated partial thromboplastin time (APTT), prothrombin time (PT), prothrombin complex, (PK), assay, factor VIII and fibrin D-dimer were determined in compliance with manufacturers recommendations using the following reagents; PTT Automate, Diagnostica Stago, Asnieres-sur- Seine, France; Thromborel® S, Behring Diagnostics GmbH, Marburg, Germany; PK-reagent GHI 129, Global Hemostasis Institute MGR, Linköping, Sweden; and Coamatic® Factor VIII, Chromogenix, Mölndal, Sweden. The tests were performed on an Automated Coagulation Laboratory instrument, ACL, model 810 (Instrumentation Laboratory, Milan, Italy).

The blood was collected from the antecubital vein by drawing 4.5 mL Monovette® (Sarstedt, Nümbrect, Germany) tube which contained 0.5 mL of anti-coagulant. The Monovette® tubes contain anti-coagulant according to prior art. For various experiments with anti-coagulants according to the invention, Monovette® tubes were opened, the original anti-coagulant discarded, the tubes rinsed with 0.15 M NaCl and filled with 0.5 mL of the anti-coagulant of choice. Plasma was obtained by centrifugation of 2 mL anti-coagulated blood for 3 minutes at 8000×g and transfer of the plasma to plastic tubes, which, in some experiments, were stored up to twenty days at −70° C. prior to analysis. For Example 7, plasma, anti-coagulated with citrate, with labeling revealing identity removed, from 22 healthy individuals and from 120 patients were kind gifts from the Department of Clinical Chemistry and Laboratory of Clinical Chemistry, University Hospital, Linköping, courtesy of Dr. Tomas Lindahl. Prior to analysis, the plasmas from healthy individuals were stored for about six months at −70° C. Plasmas from the patients were analyzed within six hours of collection.

Trisodium DL-iso-citrate, phthalic acid, 2,6-diaminopurine (hemisulfate salt), trans-aconitic acid, tricarballylic acid, and adenine were products I-1252, P-2944, D-3289, A-7376, T-9251, and A-8626, respectively, from Sigma Chemical Co. St Louis, Mo. $CaCl_2$, citric acid and oxalic acid were products 2382, 244 and 495, respectively from Merck, Darmstadt, Germany. Tri-sodium citrate was product 32320 from Riedel-de Haën, Seelze, Germany, ethyl acetate, product 10108, from BDH, England, methylmalonic acid, product 17503 43, from Fluka AG, Buchs SG, Switzerland, dimethylmalonic acid, product D16 800-9, from Aldrich-Chemie, Steinheim, Germany. Iminodiacetate product number I 120-0 was from Ega-Chemie KG, Steinheim bei Heidenheim, Germany.

Iso-citric acid was prepared, at 36% yield, by dissolving tri-sodium iso-citrate in minimal amount diluted hydrogen chloride, pH between zero and one, 5 times repeated extraction with ethyl acetate and drying. Bovine plasma deficient in vitamin K dependent coagulation factors and thromboplastin from rabbit brain were the corresponding components from PK-reagent GHI 129 detailed above. $Ca^{2+}$ activity and pH in plasma were determined potentiometrically with an ICA 2 (Radiometer, Copenhagen, Denmark) apparatus.

EXAMPLE 1

In order to identify compounds that could function as buffers for $Ca^{2+}$ at physiological levels, i.e. at about 1.3 mM of $Ca^{2+}$, water soluble compounds, either with reported dissociation constants in the range of 0.5 to 5 mM or otherwise appearing interesting, were experimentally investigated. Below, these compounds are referred to as $Ca^{2+}$ ligands or simply ligands. Experiments described below were performed to deduce the apparent dissociation constants under physiological like conditions and at ligand concentrations meaningful for $Ca^{2+}$ buffering.

Solution of 200 mM of ligand containing 20 mM of Hepes was adjusted to pH 7.4 and mixed with an equal volume of 100 mM of $CaCl_2$ solution. These mixtures were diluted 1:2, 1:4, 1:8 and 1:16 with 0.15 mM of NaCl. For all mixtures and dilutions with $Ca^{2+}$ activity below 10 mM and pH between 7.0 to 7.6, the $Ca^{2+}$ activity and pH was potentiometrically determined. From the experimentally determined $Ca^{2+}$ activity and the stoikiometric levels of ligand and $Ca^{2+}$, the apparent dissociation constant for a putative Ca*ligand complex was determined as the average of all available data. For each ligand, this average and SD, the number of determinations that were averaged (n) and published estimates are given in Table I.

TABLE I

| Ligand | kd ± S.D. (mM) | n | published estimate (mM) |
|---|---|---|---|
| methylmalonate | 22 ± 3 | 3 | 22.4 (in 0.1 M $NaClO_4$) |
| oxalate (precipitated) | | | 5.0 (in 0.1 M $KNO_3$) |
| iminodiacetate | 29 ± 12 | 2 | 8.1 (in 1 M $KNO_3$) |
| dimethylmalonate | 25 ± 73 | | 30.2 (in 0.1 M $NaClO_4$) |
| phthalate | 26 ± 73 | | 3.9 (in 0.1 M KCl) |
| 2,6-diaminopurine | 50 ± 24 | 2 | 1.6 (in 0.1 M $KNO_3$) |
| adenine | 70 ± 40 | 2 | 1.1 (in 0.1 M $KNO_3$) |
| trans-aconitate | 29 ± 53 | | |
| tricarballylate | 22 ± 53 | | |
| iso-citrate | 4.5 ± 0.6 | 5 | |
| citrate | 0.5 ± 0.05 | 4 | 0.58 |

The experiments indicate, that in our hands, citrate and iso-citrate were the only two compounds identified that formed complexes with apparent dissociation constants near the physiological $Ca^{2+}$ activity level, i.e. about 1.5 mM. These two ligands were further investigated as $Ca^{2+}$ buffering substances and as anti-coagulants. It is, however, more than likely that other ligands with required affinity can be found. Particularly, it is within the scope of the invention to investigate derivatives, e.g. methylated, halogenated, nitrated and hydroxylated, of the substances mentioned above. Most particular, derivatives of citrate with electrophilic groups, i.e. derivatives where fluoride, chloride or nitrate have been attached to the tri-carboxyl carbon skeleton, may have the required properties. The rational for this is that electrophilic groups will reduce the electron density of the carboxyls and thereby reducing their ability to interact with $Ca^{2+}$.

For several ligands, e.g. methylmalonate, dimethylmalonate and citrate, our estimates of dissociation constants were similar to published values. For other ligands, particularly phthalate, 2,6-diaminopurine and adenine, the published values are one order of magnitude and more in deviation with what observed. Perhaps the ligands at higher concentrations form complex that have reduced affinity for $Ca^{2+}$, in any case they are useless for the present context.

EXAMPLE 2

In experiments described in Example 6, it became evident that citrate and, to a lesser extent, iso-citrate are in themselves, and not only by virtue of their $Ca^{2+}$ binding, inhibitory to coagulation reactions in blood. This gave rise to the idea that these substances could perform as anticoagulants also at near physiological levels of $Ca^{2+}$ activity. For this reason, $CaCl_2$ solution was added to solutions of citrate and iso-citrate in order to make solutions of these $Ca^{2+}$ binding substances with physiological levels of $Ca^{2+}$. This was possible with iso-citrate but not with citrate. Solutions with both citrate and $CaCl_2$ formed precipitates. The following therefore only describes experiments with iso-citrate.

Nine parts (4.5 mL) of blood from one individual was drawn into four evacuated plastic containers with one part (0.5 mL) of anti-coagulant. The anti-coagulant was solutions of 0.3, 0.4, 0.6 or 0.8 M tri-sodium iso-citrate with sufficient amounts of dissolved $CaCl_2$ to give a $Ca^{2+}$ activity of about 1 mM. In the Tables II and III, the anti-coagulated blood samples are denoted by their respective content of anti-coagulant, i.e. as 30, 40, 60 and 80 mM iso-citrate.

From each container, within 15 minutes of collection, about 2 mL of the anti-coagulated blood was withdrawn using a thin hypodermic needle stuck through the elastic membrane of the container to minimize gas exchange with the surroundings. This blood was immediately centrifuged for 3 minutes at 10,000×g to pellet the blood cells and to secure about 0.8 mL of plasma. Apart from the small quantity used for determination of $Ca^{2+}$ activity and pH, see Tables II and III, this plasma was transferred to a polystyrene tube. In the Tables II and III, the various plasma and blood products are indicated by the amount of anti-coagulant in the blood, i.e. as 30, 40, 60 or 80 mM iso-citrate. (The actual levels of anti-coagulants in the plasma products are about 1.4 fold higher than in the blood products as deduced from reports on citrate content in plasma from citrate anti-coagulated blood.)

The blood products, in their original containers, and the corresponding plasma products, in capped 3 mL polystyrene tubes, were stored at room temperature and regularly inspected for presence of coagulum. In the Tables II and III coagulum formation is indicated by a capital C and no coagulum is indicated by NC. The time intervals given in the Tables indicate the time periods at which the observations were made. Results for the blood and in the plasma are given in the Tables II and III, respectively.

TABLE II

Blood

| Iso-citrate (mM) | $Ca^{2+}$/pH | 0–1 hour | 1–5 hours | 5–24 hour | 24–48 hours |
|---|---|---|---|---|---|
| 30 | 1.00/7.37 | C | C | C | C |
| 40 | 0.95/7.35 | NC | C | C | C |
| 60 | 0.98/7.33 | NC | NC | NC | NC |
| 80 | 0.97/7.33 | NC | NC | NC | NC |

TABLE III

Plasma

| Iso-citrate (mM) | $Ca^{2+}$/pH | 0–1 hour | 1–5 hours | 5–24 hour | 24–48 hours |
|---|---|---|---|---|---|
| 30 | 1.00/7.37 | NC | NC | C | C |
| 40 | 0.95/7.35 | NC | NC | NC | NC |
| 60 | 0.98/7.33 | NC | NC | NC | NC |
| 80 | 0.97/7.33 | NC | NC | NC | NC |

The results from the above described experiments with iso-citrate show that it is possible, according to the invention, to anti-coagulate a biological fluid, particularly blood and blood plasma, with substances like iso-citrate, that has a limited affinity towards $Ca^{2+}$, without reducing the $Ca^{2+}$ activity of the fluid. The typical physiological $Ca^{2+}$ activity of extra-cellular biological fluids is about 1.2 mM. Substances with moderate $Ca^{2+}$ affinity are defined as those which form complexes with $Ca^{2+}$ which are characterized by having dissociation constants of 0.8 to 8 mM at physiological conditions, i.e. temperature of about 37° C., pH of about 7.3 and ionic strength of about 150 mM.

The results indicate that substance with moderate $Ca^{2+}$ affinity, and most likely also substances with higher affinity for $Ca^{2+}$, have a mechanism of action that is hitherto not described, or at least feebly recognized. This anti-coagulative mechanism works directly on the substances of the biological fluids involved in the coagulation processes, and not via reduction of the $Ca^{2+}$ activity. The $Ca^{2+}$ activity reduction being the generally recognized mechanism of anti-coagulative action assigned to the group of calcium binding anti-coagulative substances. It is obvious from the results shown above, that, at near physiological levels of $Ca^{2+}$ activity, the substances with moderate $Ca^{2+}$ affinity are more efficient in anti-coagulating plasma than blood, i.e. less anti-coagulative substance is needed to anti-coagulate plasma.

EXAMPLE 3

Experiments are performed in a similar way as in Example 2. Nine parts of blood are collected in evacuated plastic containers with one part anti-coagulant solution. The various anti-coagulant solutions were tri-sodium iso-citrate in the range of 50 to 300 mM dissolved in water which resulted in iso-citrate levels in the range of 5 to 30 mM in the collected blood. Shortly after collection, small amounts of anti-coagulated blood were withdrawn from the containers, and $Ca^{2+}$ activity and pH were determined. The original containers with anti-coagulated blood were stored at room temperature and regularly inspected for presence of coagulum, i.e. coagulated material or clot. Denotations are as in Example 2, 'C' for coagulum and 'NC' for no coagulum etc. The results are shown in Table IV.

TABLE IV

Blood

| Iso-citrate (mM) | $Ca^{2+}$ | pH | 0–1 hour | 1–5 hours | 5–24 hour | 24–48 hours |
|---|---|---|---|---|---|---|
| 5 | 0.43* | 7.64* | C | C | C | C |
| 10 | 0.27* | 7.64* | C | C | C | C |
| 13 | 0.21* | 7.65* | C | C | C | C |
| 15 | 0.20 | 7.60 | NC | C | C | C |
| 20 | 0.18 | 7.46 | NC | NC | NC | NC |
| 25 | 0.15 | 7.46 | NC | NC | NC | NC |
| 30 | 0.12 | 7.45 | NC | NC | NC | NC |

*determined in serum

From the results above, it appears that 20 mM of iso-citrate is the minimal amount needed to anti-coagulate blood over an extended period of time. The $Ca^{2+}$ activity in the anti-coagulated blood is 0.18 mM which is about 10 fold higher than that of blood with 13 mM of tri-sodium citrate, i.e. blood collected in containers with ⅑ volume of 0.13 M of tri-sodium citrate according to the prior art. From the results in Example 2 it may be assumed that anti-coagulation of blood plasma would have required less iso-citrate anti-coagulant.

Within the scope of the invention, it is anticipated that the anti-coagulation brought about by iso-citrate can be enhanced by addition of citrate or by reducing the pH. Reduction of pH can be accomplished by using iso-citric acid or citric acid instead of sodium, potassium or lithium salts. Results from experiments performed as described above, except that the anti-coagulant is mixtures of (Na+) iso-citrate, (Na+)citrate, (H+)iso-citrate and/or (H+)citrate are summarized in Tables V, VI and VII.

TABLE V

Blood
Anti-coagulation with mixtures of (Na+)isocitrate and (Na+)citrate. The sum of the concentrations is 13 mM in the blood. The proportion citrate is in percent.

| Citrate (%) | $Ca^{2+}$ | pH | 0–1 hour | 1–5 hours | 5–24 hour | 24–48 hours |
|---|---|---|---|---|---|---|
| 20 | 0.14 | 7.48 | NC | NC | NC | NC |
| 40 | 0.09 | 7.47 | NC | NC | NC | NC |

TABLE VI

Anti-coagulation with 13 mM mixtures of (H+)isocitrate and (H+)citrate

| Citrate (%) | $Ca^{2+}$ | pH | 0–1 hour | 1–5 hours | 5–24 hour | 24–48 hours |
|---|---|---|---|---|---|---|
| 0 | 0.27 | 6.54 | NC | NC | NC | NC |
| 2.5 | 0.25 | 6.39 | NC | NC | NC | NC |
| 5 | 0.23 | 6.47 | NC | NC | NC | NC |
| 10 | 0.20 | 6.47 | NC | NC | NC | NC |

TABLES VII

Anti-coagulation with 11 mM mixtures of (H+)isocitrate and (H+)citrate

| Citrate (%) | Ca2+ | pH | 0–1 hour | 1–5 hours | 5–24 hour | 24–48 hours |
|---|---|---|---|---|---|---|
| 0 | 0.34 | 6.91 | NC | C | C | C |
| 2.5 | 0.29 | 6.63 | NC | C | C | C |
| 5 | 0.27 | 6.68 | NC | C | C | C |
| 10 | 0.22 | 6.61 | NC | C | C | C |
| 20 | 0.16 | 6.65 | NC | NC | NC | NC |
| 40 | 0.09 | 6.59 | NC | NC | NC | NC |

EXAMPLE 4

The following will demonstrate that blood, anti-coagulated according to the invention, is more stabile with regard to coagulation reactions. Therefore, blood and blood plasma, anti-coagulated according to the invention, are better suited for coagulation analysis than blood anti-coagulated according to prior art methods.

Three different types of blood collecting tubes, all drawing 4.5 mL of blood, were prepared. These three types of blood collecting tubes were denoted Citrate, Isocitrate and Citrate/Isocitrate Mixture. The tube Citrate was according to prior art and contained 0.5 mL of 0.13 M tri-sodium citrate. The tube Iso-citrate was according to the invention and contained 0.5 mL of 0.2 M tri-sodium iso-citrate. The tube iso-citrate/Citrate Mixture was also according to the invention and contained 0.5 mL of 0.078 M tri-sodium iso-citrate and 0.052 M tri-sodium citrate.

Within a time span of less than five minutes, blood from the same individual was drawn into one of each blood collecting tube Citrate, Iso-citrate and Iso-citrate/Citrate Mixture.

With a minimum of time delay, 1 mL of anti-coagulated blood was withdrawn from each of the three blood collection tubes. The blood was centrifuged for three minutes at 5000×g. As quickly as possible, about 0.4 mL of plasma was secured and analyzed for coagulation factor VIII clotting activity, activated partial thromboplastin time (APTT) and prothrombin time (PT). These analytical results were obtained within 20 minutes of blood collection and are, in the following and in FIGS. 1, 2 and 3, referred to as initial values.

The remaining blood was stored at room temperature in the three blood collecting tubes. The tubes were closed to prevent loss by evaporation. At 5 hours, 24 hours and 48 hours after blood collection, as described above, blood was withdrawn, plasma secured and plasma analyzed. The results of these analyses, expressed in relationship to the initial values, are displayed in FIGS. 1, 2 and 3.

Figure 1:
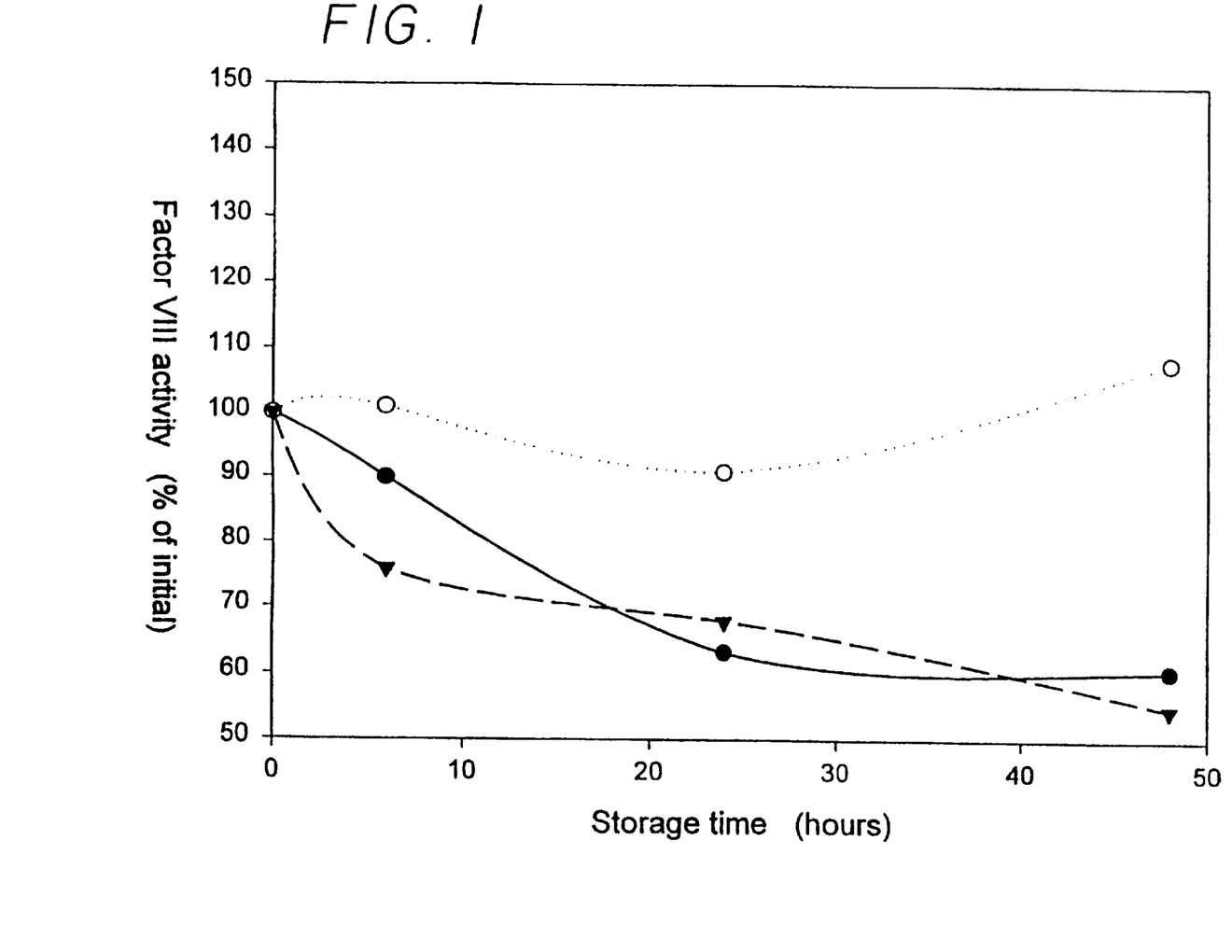
FIG. 1. Stability of factor VIII:C activity in blood collected on a blend containing 0.05 mol/L citrate and 0.08 mol/L iso-citrate (filled circle), 0.20 mol/L iso-citrate (empty circle) and on 0.13 mol/L citrate (triangle). Factor VIII:C activity was determined in plasma isolated after 0.5 hours, 6 hours, 1 day and 2 days from blood stored at room temperature. The experimental points represent the mean of results with blood from 5 subjects.

FIG. 1 shows that Factor VIII clotting activity is more stabile in blood anti-coagulated according to the invention. Particularly, blood collected according to the invention, in the tube denoted iso-citrate, showed good stability over the 48 hours of room temperature storage and the Factor VIII clotting activity was within 10% of the initial value. Blood anti-coagulated according to prior art, in the tube denoted Citrate, fell rapidly to 75% of initial activity during the first 5 hours and then continued to fall reaching 55% at 48 hours. Compared to blood anti-coagulated according to prior art, blood anti-coagulated according to the invention in the tube denoted Iso-citrate/Citrate Mixture displayed better factor VIII stability during the first 15 hours of storage and after that about the same.

Figure 2:
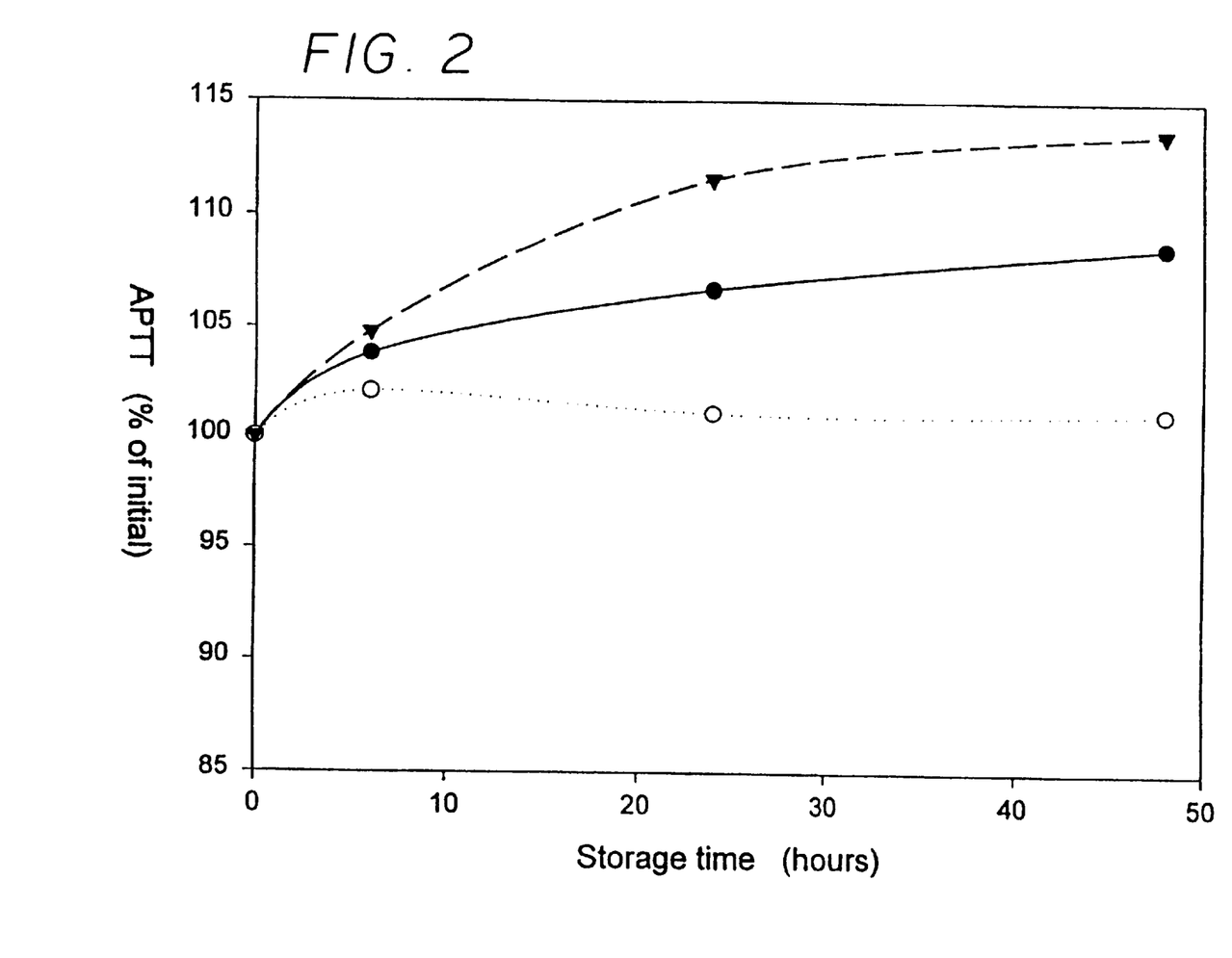
FIG. 2. Stability of activated partial thromboplastin time, APTT, in blood collected on a blend containing 0.05 mol/L citrate and 0.08 mol/L iso-citrate (filled circle), 0.20 mol/L iso-citrate (empty circle) and on 0.13 mol/L citrate (triangle). APTT was determined in plasma isolated after 0.5 hours, 6 hours, 1 day and 2 days from blood stored at room temperature. The experimental points represent the mean of results with blood from 5 subjects.

FIG. 2 shows that APTT is more stabile in blood anti-coagulated according to the invention than in blood anti-coagulated according to prior art. During 48 hours at room temperature, blood stored in the tube Iso-citrate shows an APTT within 5% of initial value. Blood stored in the tube Citrate showed an APTT increasing to 113%. Blood stored in the tube Iso-citrate/Citrate Mixture showed an APTT with intermediate stability.

Figure 3:
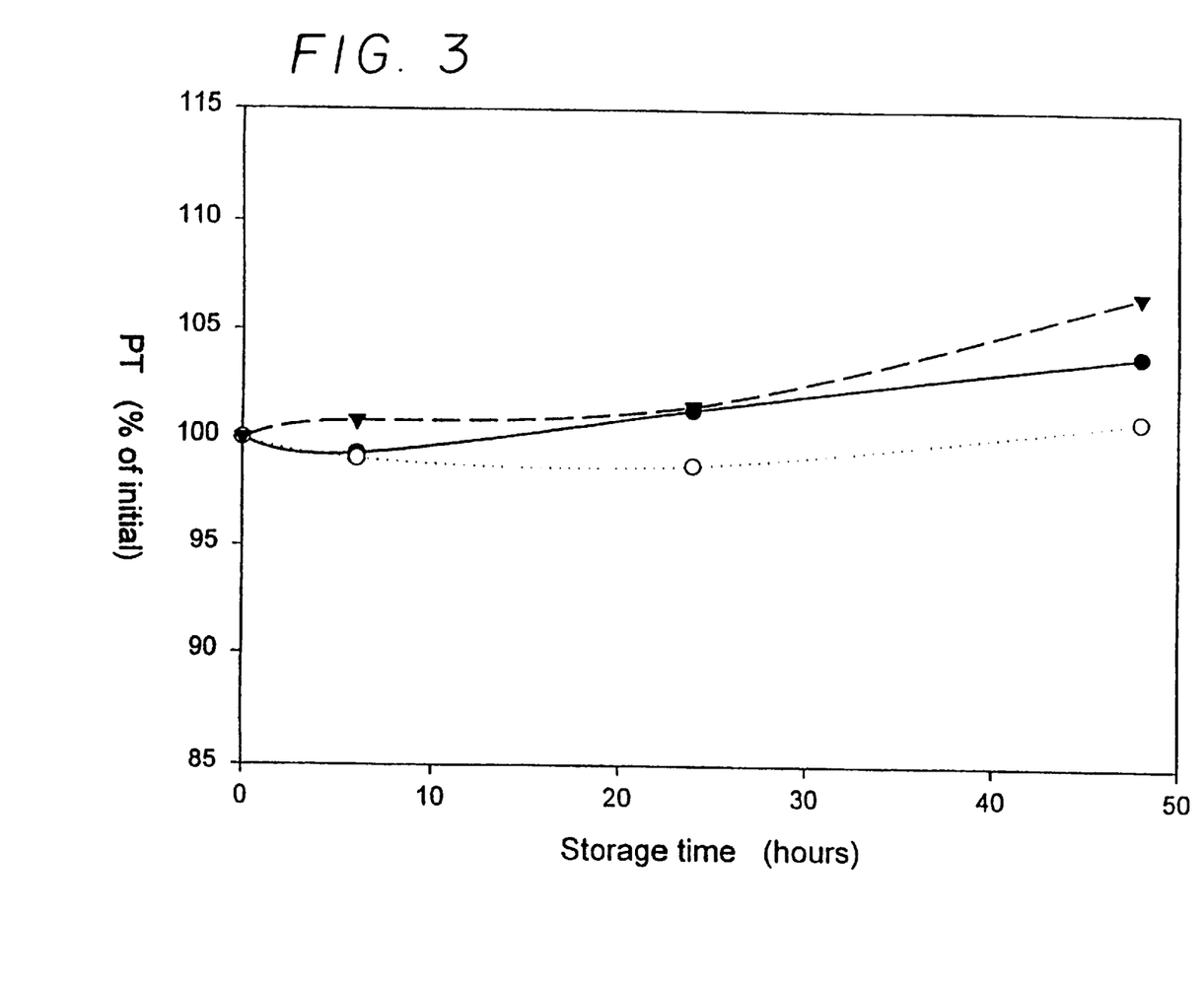
FIG. 3. Stability of prothrombin time, PT, in blood collected on a blend containing 0.05 mol/L citrate and 0.08 mol/L iso-citrate (filled circle), 020 mol/L iso-citrate (empty circle) and on 0.13 mol/L citrate (triangle). PT was determined in plasma isolated after 0.5 hours, 6 hours, 1 day and 2 days from blood stored at room temperature. The experimental points represent the mean of results with blood from 5 subjects.

FIG. 3 shows that PT is more stabile in blood anti-coagulated according to the invention. In the tube Iso-citrate the PT is within 2% of initial values, in the tube Iso-citrate/Citrate Mixture within 4% and in the tube Citrate within 7%.

EXAMPLE 5

Coagulation analysis of blood and blood plasma are performed in many different ways. Most such analysis have the following in common. Samples of blood or blood plasma are, according to prior art, anti-coagulated with citrate or, according to the present invention, with iso-citrate. The anti-coagulated blood or blood plasma is mixed with reagents that contain $Ca^{2+}$ ions which will restore and counteract the $Ca^{2+}$ lowering effect of the anti-coagulants in the sample. Since the $Ca^{2+}$ activity strongly effects the coagulation reactions and hence the results of the analysis, it is important that the Ca2+ activity is maximally well defined. I.e. the variation in $Ca^{2+}$ activity in the mixture of sample and reagent should be as small as possible. The size of this variation will be decided by the $Ca^{2+}$ buffering capacity of the sample. This buffer capacity is the stoichiometric change in $Ca^{2+}$ per liter of solution divided by the change in $Ca^{2+}$ activity. This $Ca^{2+}$ buffer capacity was determined in a system composed of sample, bovine plasma deficient in vitamin K dependent coagulation factors and rabbit brain thromboplastin. Such analytical systems are used to measure prothrombin complex activity (PK activity) since the system is sensitive to the combined activity of coagulation factors VII, X and II (the prothrombin complex factors) of the system. Such a system was modified in the present example by either addition of citrate or by addition of iso-citrate. The system was modified either by addition of 5 or 10 mM, final concentration, of the calcium ion binding substances. For each level of addition, the calcium ion buffering capacity of the analytical system was determined. The buffer capacity was determined at $Ca^{2+}$ activity in the range of 1 to 4 mM. Results for final addition of 5 mM citrate or iso-citrate are shown in FIG. 4 and for 10 mM in FIG. 5.

Figure 4:
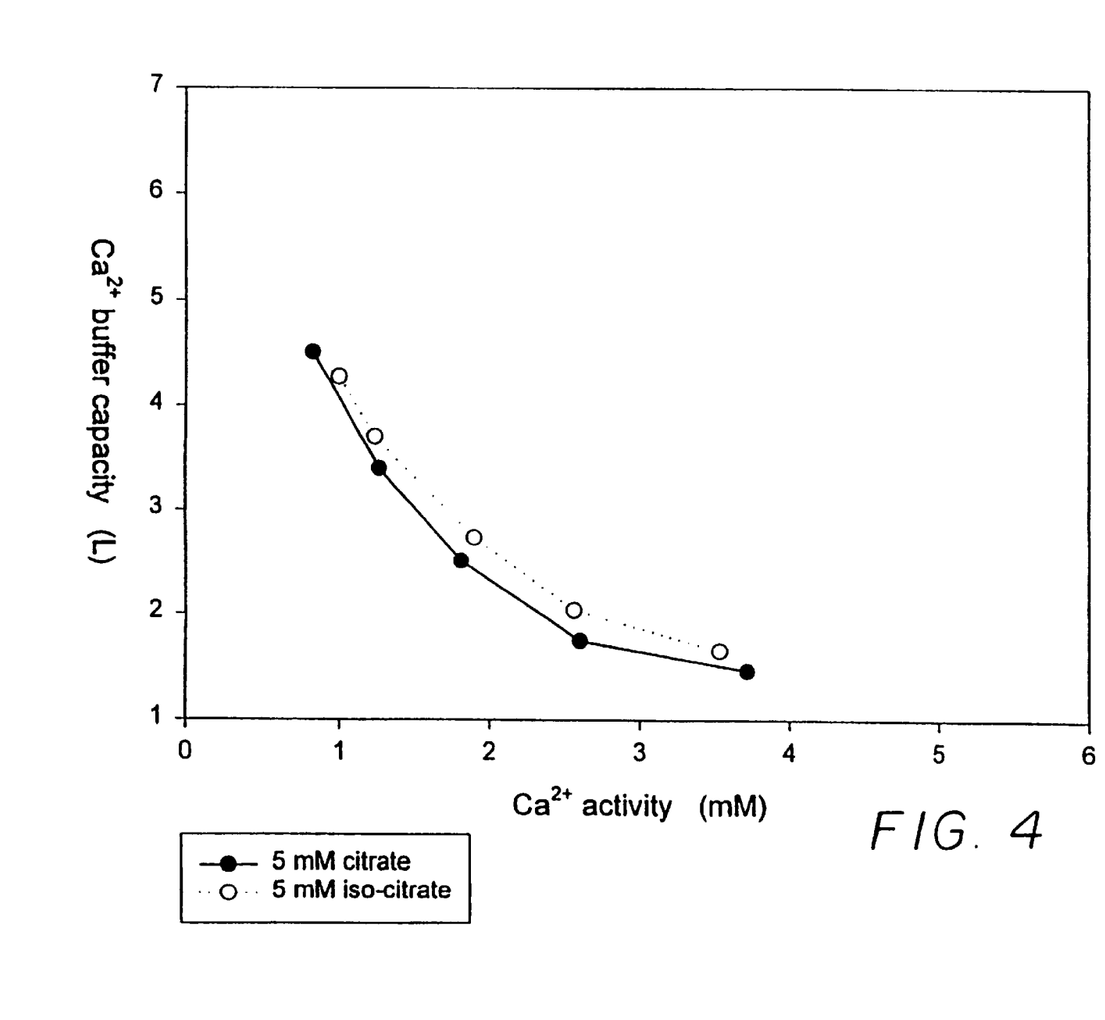
FIG. 4. $Ca^{2+}$ buffering capacity of a system used for coagulation analysis. The buffer capacity was determined at $Ca^{2+}$ activity in the range of 1 to 4 mM. Results are for final addition of 5 mM citrate or iso-citrate.
Figure 5:
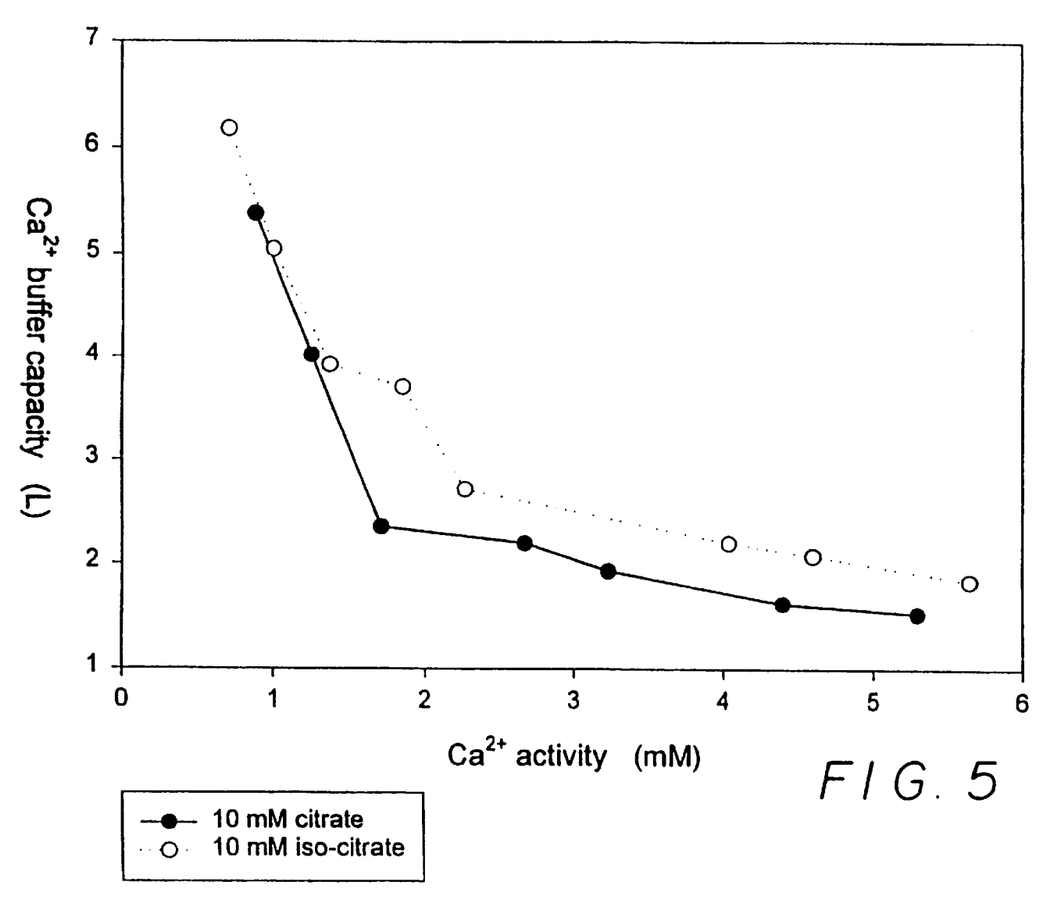
FIG. 5. $Ca^{2+}$ buffering capacity of a system used for coagulation analysis. The buffer capacity was determined at $Ca^{2+}$ activity in the range of 1 to 4 mM. Results are for final addition of 10 mM citrate or iso-citrate.

FIGS. 4 and 5 show that iso-citrate has a greater effect than citrate in increasing the $Ca^{2+}$ buffering capacity of a system used for coagulation analysis. The increased $Ca^{2+}$ buffering capacity is most obvious when the $Ca^{2+}$ activity is above 1 mM which includes the important $Ca^{2+}$ activity level of 1.3 mM which is the physiological level.

EXAMPLE 6

The assay response of the system described in Example 5 is investigated. Sample, reagent and $CaCl_2$ solution are mixed. The coagulation time is recorded. And after compacting of the coagulum by centrifugation for 3 minutes at 10,000×g, the Ca2+ activity is determined. To the reagent is added some amount of either citrate or iso-citrate. The amount of added citrate or iso-citrate is such that the final concentration of such added substances is 5 10 or 20 mM. Experiments are performed at several levels of $CaCl_2$ so that the $Ca^{2+}$ activity level of the system is varied stepwise in the range 0.7 and 9 mM.

Figure 6:
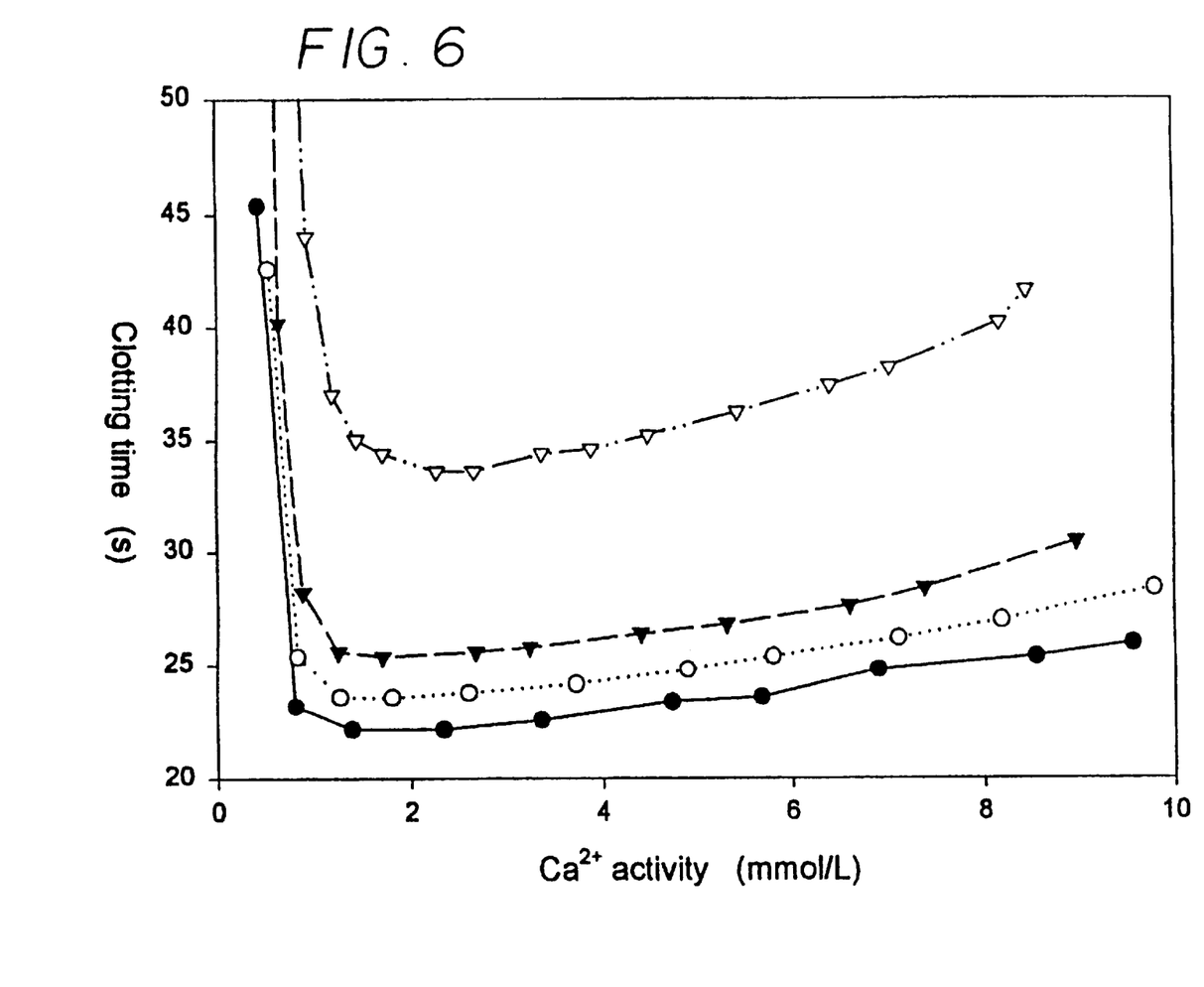
FIG. 6. Prothrombin complex (PK) time for added citrate in PK system, no citrate (filled circle), 5 mmol/L citrate (empty circle), 10 mmol/L citrate (filled triangle) and 20 mmol/L citrate (empty triangle). Calcium activity was determined potentiometrically for each data point. The experimental points represent a pooled plasma.

FIG. 6 shows how the coagulation time (KT) depends on the $Ca^{2+}$ activity. This is shown for zero, 5, 10 and 20 mM of added citrate. The same experiment performed with addition of zero, 5, 10 and 20 mM iso-citrate is shown in FIG. 7.

Figure 7:
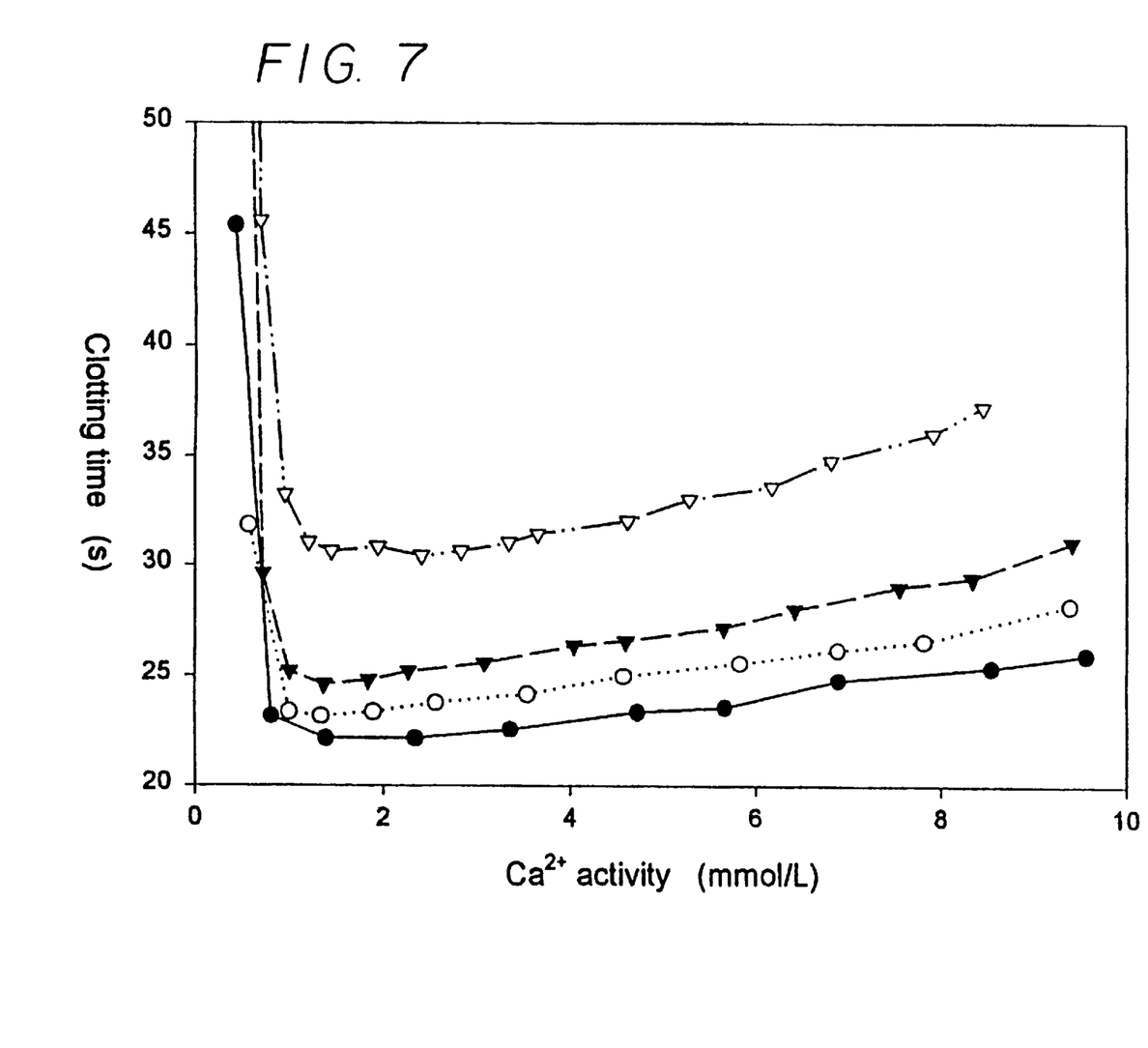
FIG. 7. Prothrombin complex (PK) time for added iso-citrate in PK system, no iso-citrate (filled circle), 5 mmol/L iso-citrate (empty circle), 10 mmol/L iso-citrate (filled triangle) and 20 mmol/L iso-citrate (empty triangle). Calcium activity was determined potentiometrically for each data point. The experimental points represent a pooled plasma.
Figure 8:
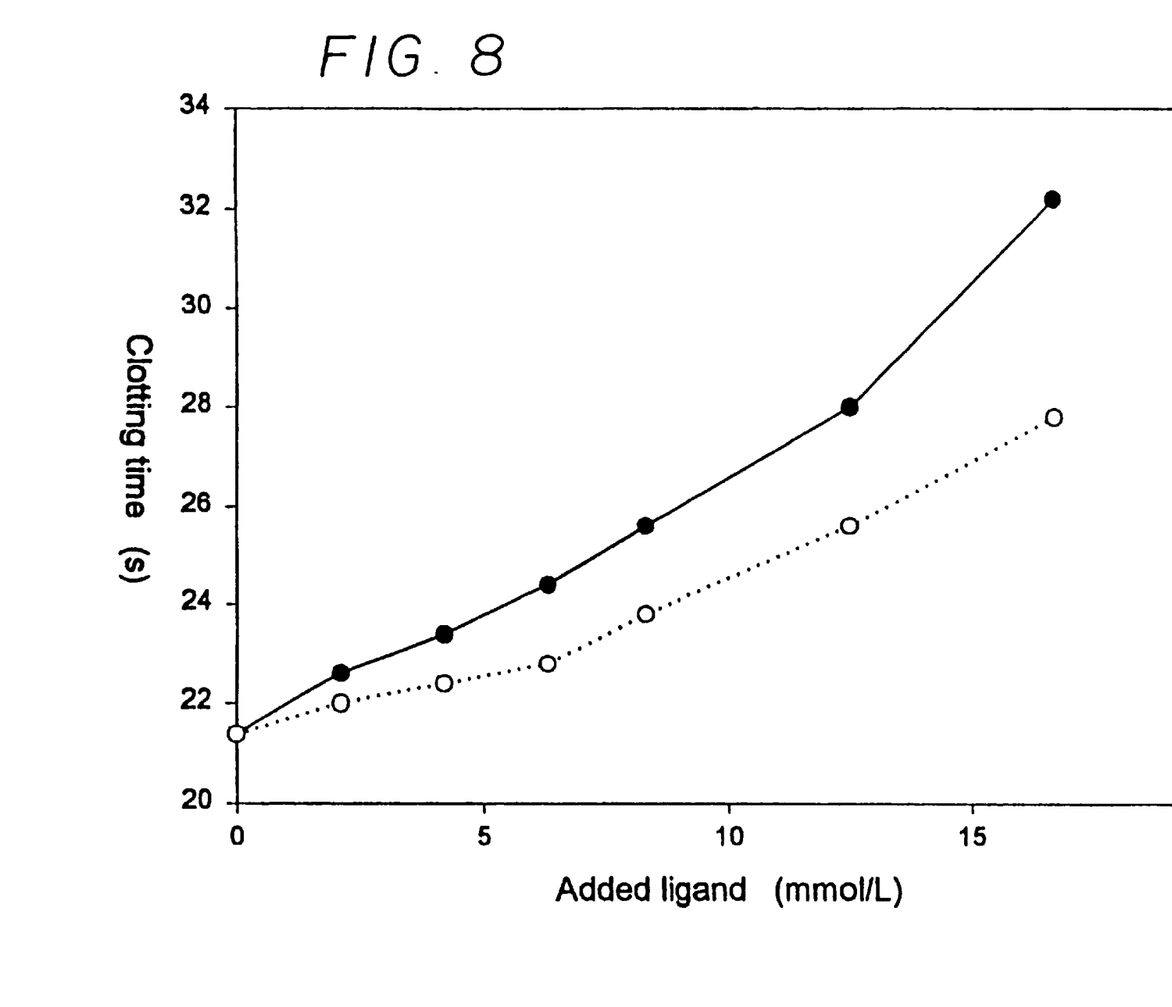
FIG. 8. Prothrombin complex (PK) time for added ligand in PK system, citrate (filled circle) and iso-citrate (empty circle). Calcium activity was about 2 mmol/L for each data point. The experimental points represent a pooled plasma.

Inspection of FIGS. 6 and 7 shows that both citrate and iso-citrate inhibit coagulation at all $Ca^{2+}$ activity levels. However, the inhibiting effect is smaller for iso-citrate than for citrate. This becomes very clear if the coagulation time at one $Ca^{2+}$ activity level is plotted against the added final concentration of citrate or iso-citrate. For $Ca^{2+}$ activity of 1.5 such a plot is seen in FIG. 8. FIG. 8 shows that citrate is about twice as inhibitory as iso-citrate per molar unit.

EXAMPLE 7

An APTT analysis performed in two steps. In the first step, one volume citrate anti-coagulated plasma is mixed with one volume activator/cephalin solution and the mixture incubated for five minutes. In the second step, one volume of 25 mM $CaCl_2$ solution is added and coagulation time registered. Such an assay was modified according to the invention by use of 25 mM $CaCl_2$ solution which also contained 30 mM iso-citrate. In the following the activator/cephalin solution and 25 mM $CaCl_2$ solution will be referred to as original APTT reagent and the activator/cephalin solution and 25 mM $CaCl_2$ solution with 30 mM iso-citrate as modified APTT reagent.

The calcium ion activity in the two step solution, i.e. the final calcium ion activity, is 2.73±0.20 mM with original APTT reagent and 1.60±0.07 mM with the modified.

With both original and modified APTT reagent, citrate anti-coagulated plasma from 22 normal persons and 120 patients were analyzed. The mean coagulation time and the SD for the healthy individuals is 32.5±3.0 seconds with the original APTT reagent and 4.4±4.6 seconds with the modified. With these mean and SD values, the deviation form the normal is calculated for the patients by subtracting the mean normal APTT from patient APTT and dividing the difference with the normal SD.

With the original APTT the mean deviation from the normal and its SD is 3.6±5.0. With the modified APTT reagent the corresponding value is 4.3±5.7. This difference is highly statistically significant according to analysis by two-tailed Student's t-test, p<0.006. Thus, patient APTT shows greater deviation from normal with an APTT reagent according to the invention than with an APTT reagent according to prior art.

What is claimed is:

1. A method of anti-coagulating blood or blood plasma or synovial fluid comprising contacting the blood or blood plasma or synovial fluid with an amount of iso-citrate so that the final concentration of isocitrate is 15–50 mM in blood and 25–70 mM in blood plasma or synovial fluid.

2. The method according to claim 1, wherein the calcium ion concentration of the anti-coagulated blood or blood plasma or synovial fluid is adjusted up to a physiological level of 1.3 mM by addition of a soluble calcium salt.

3. The method according to claim 1, wherein the anti-coagulating effect of iso-citrate is enhanced or the anti-coagulating amount of iso-citrate is reduced by addition of citrate or a pH lowering substance selected from iso-citric acid and citric acid.

4. The method according to claim 2, wherein the anti-coagulating effect of iso-citrate is enhanced or the anti-coagulating amount of iso-citrate is reduced by addition of citrate or a pH lowering substance selected from iso-citric acid and citric acid.

5. An anti-coagulated blood or blood plasma or synovial fluid containing an amount of iso-citrate so that the final concentration of isocitrate is 15–50 mM in blood and 25–70 mM in blood plasma or synovial fluid.

6. The anti-coagulated blood or blood plasma or synovial fluid according to claim 5 which further contains a soluble calcium salt in an amount adjusting the calcium ion concentration of the anti-coagulated blood or blood plasma or synovial fluid up to a physiological level of 1.3 mM.

7. The anti-coagulated blood or blood plasma or synovial fluid according to claim 5, wherein the amount of iso-citrate is reduced due to addition of a pH lowering amount of citrate or a pH lowering substance selected from iso-citric acid and citric acid.

8. The anti-coagulated blood or blood plasma or synovial fluid according to claim 6, wherein the amount of iso-citrate is reduced due to addition of a pH lowering amount of citrate or a pH lowering substance selected from iso-citric acid and citric acid.

* * * * *